United States Patent [19]

Vernon

[11] Patent Number: 4,999,187

[45] Date of Patent: Mar. 12, 1991

[54] HAIR TREATMENT COMPOSITION AND METHOD

[76] Inventor: Della M. Vernon, 1641 N. Hillside, Wichita, Kans. 67214

[21] Appl. No.: 361,434

[22] Filed: Jun. 5, 1989

[51] Int. Cl.$^5$ .......................... A61K 7/06; A61K 7/075
[52] U.S. Cl. ........................................ 424/70; 511/789
[58] Field of Search ........................... 424/70; 514/789

[56] References Cited

U.S. PATENT DOCUMENTS

| | | | |
|---|---|---|---|
| 82,660 | 9/1868 | Tilton | 424/70 |
| 376,808 | 1/1888 | Pratt | 424/70 |
| 3,932,611 | 1/1976 | McCarthur | 424/70 |
| 3,980,768 | 9/1976 | White | 424/70 |
| 4,002,734 | 1/1977 | Pickford | 424/70 X |
| 4,180,561 | 12/1979 | Vinson | 424/70 X |
| 4,237,112 | 12/1980 | Selega et al. | 424/70 |

*Primary Examiner*—Merrell C. Cashion, Jr.
*Assistant Examiner*—Susan S. Rucker

[57] ABSTRACT

A hair and scalp treatment composition comprising 60.0 wt. % or more petrolatum, 5.0 wt. % or more sulfur, 0.5 wt. % or more 1,2,3-propanetriol, and the remainder an oil. This hair and scalp treatment composition can effectively prevent dandruff in the hair while conditioning the hair and causing hair to grow in areas of the scalp where hair has ceased to grow.

5 Claims, No Drawings

HAIR TREATMENT COMPOSITION AND METHOD

Background of the Invention

1. Field of the Invention

The present invention is related to a hair treatment composition. More particularly, the present invention provides for a hair treatment composition that can cause hair to grow in areas on the scalp where hair has stopped growing, and to a method for treating hair and scalp.

2. Description of the Prior Art

A patentability investigation was conducted and the following were discovered: U.S. Pat No. 3,236,733 to Karsten et al.; U.S. Pat. No. 3,636,213 to Gerstein et al.; U.S. Pat. No. 3,778,502 to Aubin et al.; U.S. Pat. No. 3,966,928 to Douglass; U.S. Pat. No. 4,379,753 to Bolich, Jr.; U.S. Pat. No. 4,405,645 to Rothlisberger et al.; U.S. Pat. No. 4,556,554 to Calvo; U.S. Pat. No. 4,680,300 to Nelson et al.; U.S. Pat. No. 4,728,667 to Yanagi et al.; and U.S. Pat. No. 4,772,689 to Lang et al. None of the foregoing prior art patents teach or suggest the particular hair treatment and method of this invention.

SUMMARY OF THE INVENTION

The present invention accomplishes its desired objects by broadly providing a hair and scalp treatment composition comprising from about 60.0 wt. % to about 85.0 wt. % petrolatum; from about 5.0 wt. % to about 17.0 wt. % sulfur; from about 0.5 wt. % to about 5.0 wt. % 1,2,3-propanetriol; and from about 5.0 wt. % to about 34.5 wt. % of an oil selected from the group consisting of methyl salicylate, bergamot oil, sandalwood oil, mineral oil, peppermint oil, clove oil, mustard oil, citronella oil, almond oil and mixtures thereof. The present invention more particularly accomplishes its desired objects by more particularly providing a hair and scalp treatment composition comprising from about 60.0 wt. % to about 85.0 wt. % petrolatum; from about 5.0 wt. % to about 17.0 wt. % sulfur; from about 0.5 wt. % to about 5.0 wt. % 1,2,3-propanetriol; from about 0.5 wt. % to about 5.0 wt. % methyl salicylate; from about 0.5 wt. % to about 10.0 wt. % bergamot oil; from about 0.25 wt. % to about 5.0 wt. % sandalwood oil; from about 0.5 wt. % to about 10.0 wt. % cinnamon oil; from about 0.5 wt. % to about 10.0 wt. % coconut oil; from about 0.5 wt. % to about 10.0 wt. % olive oil; from about 0.5 wt. % to about 15.0 wt. % mineral oil; from about 0.5 wt. % to about 10.0 wt. % peppermint oil; from about 0.01 wt. % to about 5.0 wt. % clove oil; from about 0.5 wt. % to about 5.0 wt. % mustard oil; from about 0.25 wt. % to about 5.0 wt. % citronella oil; almond oil. The hair and scalp treatment composition is topically applied to the hair and scalp to remove dandruff and/or to bring life to hair and/or to cause hair to grow in areas on the scalp where hair has stopped growing.

DETAILED DESCRIPTION OF THE INVENTION

The hair and scalp treatment composition of this invention is for controlling dandruff while simultaneously causing hair to grow in areas on the scalp where hair has stopped growing. More particularly, the hair and scalp treatment composition of this invention is a conditioner for hair to bring "life" back to hair, while simultaneously providing for hair growth on bald spots on the scalp. The hair and scalp treatment composition broadly comprises from about 60.0 wt. % to about 85.0 wt. % petrolatum (i.e., petroleum jelly or mineral jelly); from about 5.0 wt. % to about 17.0 wt. % sulfur; from about 0.5 wt. % to about 5.0 wt. % 1,2,3-propanetriol (i.e., glycerin or glycerol); and from about 5.0 wt. % to about 34.5 wt. % of an oil selected from the group consisting of methyl salicylate (i.e., wintergreen oil), bergamot oil, sandalwood oil, cinnamon oil, coconut oil, olive oil, mineral oil, peppermint oil, clove oil, mustard oil, citronella oil, almond oil, and mixtures thereof.

Preferably, the hair and scalp treatment composition of the present invention comprises about 60.0 wt. % to about 85.0 wt. % petrolatum; from about 5.0 wt. % to about 17.0 wt. % sulfur; from about 0.5 wt. % to about 5.0 wt. % 1,2,3-propanetriol; from about 0.5 wt. % to about 5.0 wt. % methyl salicylate; from about 0.5 wt. % to about 10.0 wt. % bergamot oil; from about 0.25 wt. % to about 5.0 wt. % sandalwood oil; from about 0.5 wt. % to about 10.0 wt. % cinnamon oil; from about 0.5 wt. % to about 10.0 wt. % coconut oil; from about 0.5 wt. % to about 10.0 wt. % olive oil; from about 0.5 wt. % to about 15.0 wt. % mineral oil; from about % 0.5 wt. % to about 10.0 wt. % peppermint oil; from about 0.01 wt. to about 5.0 wt. % clove oil; from about 0.5 wt. % to about 5.0 wt. % mustard oil; from about 0.25 wt. % to about 5.0 wt. % citronella oil; and from about 0.25 wt. % to about 5.0 wt. % almond oil.

More preferably, the hair and scalp treatment composition comprises about 70 wt. % petroleum jelly; about 11 wt. % sulfur; about 1 wt. % wintergreen oil; about 2 wt. % bergamot oil; about % 0.5 wt. % sandalwood oil; about 2 wt. % cinnamon oil; about 2 wt. coconut oil; about 2 wt. % olive oil; about 4 wt. % mineral oil; about 2 wt. % peppermint oil; about 1 wt. % mustard oil; about 1 wt. % glycerin; about 0.5 wt. % citronella oil; about 0.5 almond oil; and the remainder olive oil.

The hair and scalp treatment composition is formed by heating the petroleum jelly (which may be defined as the product obtained by fractional distillation of still residues from the steam distillation of paraffin-base petroleum or from steam-reduced crude oils from which the light fractions have been removed) until it is in a liquid state. Typically, the petroleum jelly melts at a temperature of from about 38° C. to about 60° C. The sulfur and the mineral oil (which may be defined as a liquid petroleum derivative, or an oil obtained from inorganic matter, as petroleum and its products) are mixed together until a homogeneous mixture is obtained. The sulfur-mineral oil mixture may subsequently be strained to remove any lumps. After the sulfur-mineral oil mixture is formulated (and, optionally, after straining) it is added to the liquefied petroleum jelly, and the mixture is blended/mixed until a homogeneous mixture is obtained. Subsequently, the remaining ingredients (i.e., glycerin and all of the oils) are added and admixed until thoroughly mixed. Preferably, the mustard oil is the last added ingredient. After all ingredients have been mixed together, the mixture is allowed to cool to room temperature, for example 60° F. to about 80° F., while the hair and scalp treatment composition takes the form of a jell or a salve or a balm.

The invention will be illustrated by the following set forth examples which are given by way of illustration and not by any limitation. All parameters such as concentrations, mixing proportions, compounds, etc., submitted in these examples to be construed to unduly limit the scope of the hair and scalp treatment composition of this invention and the method for treating hair and scalp.

EXAMPLE I

Heat 4 to 5 lbs. of petroleum jelly (e.g. that sold under the trademark VASELINE ®) until melted. Mix 10 oz. of sulfur with 4 oz. of mineral oil until well blended. If need be, strain the sulfur-mineral oil mixture to remove lumps. Add the liquefied petroleum jelly to the sulfur-mineral oil mixture and mix thoroughly. Thereafter, add to the liquefied petroleux jelly-sulfur-mineral oil mixture the following compounds: 1 oz. oil of wintergreen; ½ to 2 oz. oil of bergamot; ½ oz. oil of sandalwood; ½ to 2 oz. cinnamon oil; 1 to 2 oz. coconut oil; 2 oz. olive oil; 1 oz. glycerin; almond oil; 1 to 2 oz. peppermint oil; 1/16 to ⅛ oz. oil of clove; 2 to 2½ tablespoons oil of mustard (preferably the mustard oil is the last ingredient added, to produce the best results).

All ingredients are completely and thoroughly mixed together and allowed to cool to room temperature to produce a jell.

The product is rubbed into the scalp with the fingers massaging the scalp. It opens up the pores of the scalp and goes into the scalp skin to produce healthy hair (i.e., brings life to hair), to prevent dandruff, while causing hair to grow in the area of previously bald spots. The product is preferably applied twice a week.

EXAMPLE II

Remove any one (or more) ingredients from the hair and scalp treatment composition of Example I and find that the results are inferior to the results produced when all ingredients are employed per Example I.

While the present invention has been described herein with reference to particular embodiments thereof, a latitude of modification, various changes and substitutions are intended in the foregoing disclosure, and it will be appreciated that in some instances some features of the invention will be employed without a corresponding use of other features without departing from the scope of the invention as set forth.

I claim:

1. A hair and scalp treatment composition comprising from about 60.0 wt. % to about 85.0 wt. % petrolatum; from about 5.0 wt. % to about 17.0 wt. % sulfur; from about 0.6 wt. % to about 5.0 wt. % 1,2,3-propanetriol; from 0.6 wt. % to about 5.0 wt. % mustard oil; and from about 5.0 wt. % to about 34.5 wt. % of an oil selected from the group consisting of methyl salicylate, bergamot oil, sandalwood oil, cinnamon oil, coconut oil, olive oil, mineral oil, peppermint oil, clove oil, citronella oil, and mixtures thereof.

2. A hair and scalp treatment composition comprising from about 60.0 wt. % to about 85.0 wt. % petrolatum; from about 5.0 wt. % to about 17.0 wt. % sulfur; from about 0.5 wt. % to about 5.0 wt. % 1,2,3- propanetriol; from about 0.5 wt. % to about 5.0 wt. % methyl salicylate; from about 0.5 wt. % to about 10.0 wt. % bergamot oil; from about 0.25 wt. % to about 5.0 wt. % sandalwood oil; from about 0.5 wt. % to about 10.0 wt. % cinnamon oil; from about 0.5 wt. % to about 10.0 wt. % coconut oil; from about 0.5 wt. % to about 10.0 wt. % olive oil; from about 0.5 wt. % to about 15.0 wt. % mineral oil; from about 0.5 wt. % to about 10.0 wt. % peppermint oil; from about 0.01 wt. % to about 5.0 wt. % clove oil; from about 0.5 wt. % to about 5.0 wt. % mustard oil;-from about 0.25 wt. % to about 5.0 wt. % citronella oil almond oil.

3. A method for treating hair and scalp comprising the steps of:
   (a) forming a treatment composition comprising from about 60.0 wt. % to about 85.0 wt. % petrolatum; from about 5.0 wt. % to about 17.0 wt. % sulfur; from 0.5 wt. % to about 5.0 wt. % 1,2,3-propanetriol; from about 0.5 wt. % to about 5.0 wt. % mustard oil; from about 0.5 wt. % to about 15.0 wt. % mineral oil; and from about 5.0 wt. % to about 34.5 wt. % of an oil selected from the group consisting of methyl salicylate, bergamot oil, sandalwood oil, cinnamon oil, coconut oil, olive oil, peppermint oil, clove oil, citronella oil, and mixtures thereof; and
   (b) applying the treatment composition of step (a) to hair and scalp.

4. The method of claim 3 wherein said forming step (a) comprises:
   (c) heating the petrolatum to a temperature of at least about 38° C. to cause the petrolatum to melt into a liquid state;
   (d) admixing the sulfur and the mineral oil together until thoroughly mixed;
   (e) adding the mixture of step (d) to the liquid petrolatum of step (c); and
   (f) adding the 1,2,3-propanetriol and the oil to the mixture of step (e) and subsequently
   (g) adding the mustard oil as the last component to be added.

5. The method of claim 4 additionally comprising straining the mixture of step (d) prior to adding to the liquid petrolatum of step (e).

* * * * *